United States Patent
Burhop et al.

(10) Patent No.: US 12,059,509 B1
(45) Date of Patent: Aug. 13, 2024

(54) METHOD AND MATRIX FOR TISSUE REGENERATION

(71) Applicant: Integra LifeSciences Corporation, Princeton, NJ (US)

(72) Inventors: Kenneth Burhop, Fallbrook, CA (US); Sunil Saini, Monroe, NJ (US); Ankur Gandhi, Metuchen, NJ (US); Angana Kharge, Hillsborough, NJ (US); Brandon Johnson, Plainsboro, NJ (US); Paul Bonvallet, Metuchen, NJ (US)

(73) Assignee: Integra LifeSciences Corporation, Princeton, NJ (US)

( * ) Notice: Subject to any disclaimer, the term of this patent is extended or adjusted under 35 U.S.C. 154(b) by 557 days.

(21) Appl. No.: 16/866,966

(22) Filed: May 5, 2020

(51) Int. Cl.
| | |
|---|---|
| *A61L 27/60* | (2006.01) |
| *A61F 2/10* | (2006.01) |
| *A61L 27/36* | (2006.01) |
| *A61L 27/48* | (2006.01) |
| *A61L 27/56* | (2006.01) |
| *A61L 27/58* | (2006.01) |

(52) U.S. Cl.
CPC ............. *A61L 27/60* (2013.01); *A61F 2/105* (2013.01); *A61L 27/362* (2013.01); *A61L 27/48* (2013.01); *A61L 27/56* (2013.01); *A61L 27/58* (2013.01); *A61F 2210/0004* (2013.01)

(58) Field of Classification Search
CPC .. A61F 2/105; A61F 2210/0004; A61L 27/60; A61L 27/362; A61L 27/56; A61L 27/48; A61L 27/58
See application file for complete search history.

(56) References Cited

U.S. PATENT DOCUMENTS

| | | | |
|---|---|---|---|
| 4,947,840 A | 8/1990 | Yannas et al. | |
| 5,326,356 A | 7/1994 | Della Valle et al. | |
| 5,650,164 A | 7/1997 | Della Valle et al. | |
| 5,658,331 A | 8/1997 | Della Valle et al. | |
| 6,969,523 B1 | 11/2005 | Mattern et al. | |
| 7,723,108 B2 | 5/2010 | Truncale et al. | |
| 8,415,159 B2 | 4/2013 | Ward et al. | |
| 8,557,581 B2 | 10/2013 | Ngo et al. | |
| 8,986,377 B2 | 3/2015 | Richter et al. | |
| 2008/0097601 A1 | 4/2008 | Codori-Hurff | |
| 2015/0366669 A1 | 12/2015 | Bartee et al. | |
| 2017/0072110 A1* | 3/2017 | Ringo .................... | A61K 35/36 |
| 2018/0250441 A1 | 9/2018 | Cornwell et al. | |

FOREIGN PATENT DOCUMENTS

WO    WO97/06837    2/1997

OTHER PUBLICATIONS

"Musculoskeletal Transplant Foundation", MTF, Edision, NJ, 2012.
(Continued)

*Primary Examiner* — Dinah Baria
(74) *Attorney, Agent, or Firm* — KDW FIRM PLLC (57) ABSTRACT

Disclosed is a method of regenerating a skin wound using a perforated dermal regeneration matrix combined with autograft in a single-stage procedure. The size of the perforations and the spacing between perforations in the dermal matrix are selected to facilitate drainage, encourage vessel growth and minimize scar tissue formation.

14 Claims, 10 Drawing Sheets

5x5x0.08 cm with 0.1cm hole (56) References Cited

OTHER PUBLICATIONS

"Strattice Matrix Perforated", LifeCell Corporation, Branchburg, NJ, 2015.

Chun, Yoon S., et al., "Single-Stage Full-Thickness Scalp Reconstruction Using Acellular Dermal Matrix and Skin Graft", Open Access Journal of Plastic Surgery, vol. 11, 28-33, Jan. 2011.

Dantzer, Eric, et al., "Using Integra Dermal Regeneration Template Single Layer Thin in practice", Wounds International 2018, vol. 9, Issue 3, 71-75, 2018.

Gabriel, Allen, et al., "Single-stage Reconstruction for Soft Tissue Defects: A Case Series", Ostomy Wound Management, 58(6), 30-37, Jun. 2012.

Jung, Sung-No et al., "One-Stage Skin Grafting of the Exposed Skull With Acellular Human Dermis (AlloDerm)", The Journal of craniofacial surgery, 19(6):1660, Abstract, www.researchgate.net, Dec. 2008.

Lyons, Mitchell, et al., "Single-Stage Dermal Matrix and Skin Grafting to Treat a Complicated Hand Wound", Eplasty. 2016; 16: ic23. www.ePlasty.com, Jun. 2016.

Simcock, Jeremy, et al., "Ovine Forestomach Matrix as a Substrate for Single-Stage Split-Thickness Graft Reconstruction", Eplasty, vol. 13, 495-502, www.ePlasty.com, Nov. 2013.

Newman, Chad, et al., "One Stage Integra(R) and Skin Grafting of Full-Thickness Human Wounds", Plastic and Reconstructive Surgery, Abstract Supplement, 2006, 140.

Suh, Hyunsuk, et al., "One Stage Allogenic Acellular Dermal Matrices (ADM) and Split-Thickness Skin Graft with Negative Pressure Wound Therapy", Chapter 4, Intech, 35-50, 2013.

Wollina, Uwe, "One-stage Reconstruction of Soft Tissue Defects with the Sandwich Technique: Collagen-elastin Dermal Template and Skin Grafts", Journal of Cutaneous and Aesthetic Surgery, 4(3), 176-185, 2011.

\* cited by examiner

5x5x0.08 cm with 0.1cm hole

FIG. 1

5x5x0.08 cm with 0.23cm holes

FIG. 2

20x25x0.08 cm with 0.1cm holes

FIG. 3

20x25x0.08 cm with 0.23cm holes

FIG. 4

Porcine wound covered with solid matrix and STSG

FIG. 5

H&E stain of integrated, viable skin graft over macro-channel

FIG. 6

1,3 Optimal (1 mm diameter x 21 + 3 mm diameter x 4)

FIG. 7A

3 mm Only (3 mm diameter x 8)

FIG. 7B

1 mm Only ( 1 mm diameter x 72)

FIG. 7C

1,3 Excess (1 mm diameter x 44 + 3 mm diameter x 9)

FIG. 7D

H&E stain of vascular structures within 1 mm channel (double arrow)
(T – matrix adjacent to channel; open arrowheads – multiple large vessels; closed arrowheads – small vessels)

FIG. 8A

H&E stain of vascular structures within 3 mm wide macro-channel.
(E – intact STSG on channel surface)

FIG. 8B

H&E stain of compacted granulation tissue within 3 mm channel (double arrow)

FIG. 9

1 mm and 3 mm spacing design on 2x2 cm² matrix

FIG. 10

Micro-CT image of Vascular network through channel

FIG. 11

Micro-CT image of day 8 scaffold

FIG. 12A

Micro-CT image of day 22 scaffold

FIG. 12B

H&E stain of vascular structures within a 1 mm channel

FIG. 13

METHOD AND MATRIX FOR TISSUE REGENERATION

FIELD OF THE INVENTION

The invention generally relates to the field of tissue regeneration. More specifically, the invention relates to methods for regenerating dermal tissue and matrices used for the methods.

BACKGROUND

Human skin has two layers: the thin, outer layer called the epidermis and the much thicker underlayer called the dermis. When damaged, the epidermis is capable of healing itself. When there is complete loss of the dermis, it heals by scar formation rather than by regeneration. Severe wounds involve the loss or damage of not only the epidermis but also the dermis.

U.S. Pat. No. 4,947,840, which is incorporated herein by reference in its entirety, discloses a biodegradable polymeric material for treating wounds, which acts as a scaffold and induces the wound to synthesize new tissue. The material preferably comprises Type-I collagen and glycosaminoglycan (GAG) in a covalently crosslinked sheet. The material has been shown to reduce contraction and scarring of dermal wounds when used in a sheet form and placed over wounds to promote regeneration.

U.S. Pat. No. 6,969,523, which is incorporated herein by reference in its entirety, describes compositions of cross-linked collagen and a glycosaminoglycan which retain characteristics rendering them useful as tissue engineering matrices or scaffolds following terminal sterilization. Such compositions may further comprise a silicone layer applied to the collagen and GAG layer. These biodegradable matrices have properties for many medical applications, particularly in the promotion of dermal regeneration.

A product commercially available on the market is INTEGRAL® Dermal Regeneration Template (Integra LifeSciences Corporation, Princeton, New Jersey, U.S.A.). The product is a bilayer membrane system designed to provide immediate wound closure and permanent regeneration of dermis. The thick underlayer is made of a porous matrix of fibers of cross-linked bovine tendon collagen and glycosaminoglycan (chondroitin-6-sulfate). This porous collagen matrix acts as a scaffold for regenerating dermal skin cells and enables the re-growth of a functional dermal layer of skin. The outer layer is made of a thin silicone film that acts like skin's epidermis. It protects the wound from infection and controls both heat and moisture loss.

Full-thickness wounds often need complex procedures for defect closures, in particular when bone, cartilage or tendons are exposed. The application of the bilayer product for deep or full-thickness wounds involves two stages. In the first stage, following excision of the patient's wound to the level of viable tissue, the bilayer template is applied to the prepared wound bed with the collagen layer facing down in direct contact with the wound bed. In the second stage, which usually occurs in a few weeks later after the dermis regenerates, the silicone layer is removed and replaced by a skin autograft, for example, an epidermal skin graft or a split-thickness skin graft (STSG) taken from another area of the patient's body. Such a two-stage method is often required to achieve epidermal closure. STSG refers to a skin graft that contains the epidermis and a portion of the dermis, which is in contrast to a full-thickness skin graft (FTSG) which consists of the epidermis and entire dermis. The area where the skin is taken from is called a donor site. The transferred skin graft will help the recipient wound site to heal, and the donor site can regrow new skin in a few weeks.

Although some dermal regeneration methods and commercial products are available, there remains a need for methods and devices that provide simplified and effective treatment to patients in need of dermal tissue repair.

SUMMARY

In a first aspect, the present invention relates generally to a method for treating skin wounds using a perforated dermal regeneration matrix in combination with a skin autograft. With this method, patients in need of treatment of deep or full-thickness wounds can be treated in a single-stage procedure, which will eliminate the need for the patient to undergo a second operative procedure weeks later and thus minimize hospital stay and reduce overall costs of treatment and care.

Examples of the present invention includes a method of treating a skin wound of a mammalian subject in need of such treatment, the method comprising the steps of providing a sheet of biodegradable porous polymeric matrix, wherein the sheet has a plurality of channels penetrating through the thickness of the sheet creating void areas on the sheet, and wherein the sheet has a void space percentage of 1% to 10%, the void space percentage being total void areas represented by the plurality of channels relative to the total area of the sheet in its intact form; cleaning the wound to provide a prepared wound bed; placing the sheet of biodegradable porous polymeric matrix to the prepared wound bed; removing a skin graft from a healthy area of the subject and placing the skin graft on top of the sheet of biodegradable porous polymeric in the wound bed; and closing the wound treated with the sheet of biodegradable porous polymeric and the skin graft.

In another aspect, the present invention relates to a sheet of biodegradable porous polymeric matrix having a plurality of pass-through channels as described in the method above.

Examples of the present invention include a tissue regeneration matrix for repairing skin wounds, comprising a porous membrane of cross-linked collagen and glycosaminoglycan matrix, the membrane having a plurality of holes regularly spaced in the membrane, wherein the holes are 0.25 mm to 3 mm in diameter and are spaced from each other by a distance between 1 mm and 25 mm; and wherein the diameter and spacing of channels are selected to maintain a void space percentage in the range of 1% and 10%.

These and other features and advantages of the invention or certain embodiments of the invention will be apparent to those skilled in the art from the following disclosure and description of exemplary embodiments.

BRIEF DESCRIPTION OF THE DRAWINGS

Embodiments of the present invention are described herein with reference to the drawings, in which:

FIGS. 8A and 8B are H&E stained histology images of vascular structures within macro-channels.

DETAILED DESCRIPTION OF THE INVENTION

The standard treatment using dermal substitutes, such as those described in U.S. Pat. No. 6,969,523, for deep or full-thickness wounds require operative procedures in two stages that are typically 2-4 weeks apart. After a bilayer dermal substitute is applied to a prepared wound bed in the first stage procedure, the initial phase of integration and imbibition begins when wound fluids invade the matrix and fibrin fosters adherence to the wound bed. Fibroblasts, lymphocytes and macrophages migrate into the matrix. Later, endothelial cells begin forming the neovascular network. As healing progresses, endogenous collagen is deposited by the fibroblasts, replacing the collagen/glycosaminoglycan layer of the dermal substitute. In the procedure of the second stage in about 3 weeks, when the neodermis has formed and vascularization is adequate, the silicone layer is removed, leaving autologous dermis in place, and then a thin skin autograft taken from a donor site is applied over the neodermis. Such two-stage procedures help minimize autograft failure and promote permanent regeneration of functional dermis at the recipient wound site, and minimize donor site wounds. Such two-stage procedures have been shown to be clinically effective, but it would be desirable to use a single-stage procedure to reduce process complexity and overall treatment costs. However, single-stage procedures, without first forming neodermis at the wound site to support skin autograft, could result in autograft loss and other failures and additional procedures might still be required to achieve epidermal closure.

The present invention provides a method of repairing deep or full-thickness wounds by applying a perforated dermal matrix in combination with a skin autograft to the wound site in a single stage procedure. Such matrix facilitates the necessary nutrient transfer to the autograft thus encouraging survival of the autograft. The size of the perforations and the spacing between perforations in the dermal matrix are carefully tailored to facilitate drainage, encourage vessel growth and minimize scar tissue formation. The one-stage can reduce the overall cost of treatment and decrease hospital stay all while providing excellent results and decreased morbidity.

The terms "perforation", "channel", "macro-channel", "fenestration" and "hole" are used herein interchangeably and refer to an aperture or hole passing through something.

The terms "skin autograft", "autograft", "skin graft", and "graft" are used herein interchangeably and means an epidermal graft, split-thickness skin graft (STSG) or full-thickness skin graft (FTSG) removed from the patient and to be applied to the same patient, including derivatives of any of the foregoing, such as skin cells and stem cells extracted therefrom and any of the foregoing that has been expanded, treated, or cultured. An epidermal graft is composed of epidermis. An STSG is composed of epidermis and a variable amount of dermis. As FTSG includes all the layers of the skin.

The terms "matrix" and "scaffold" as used herein refer to a construct of natural or synthetic polymeric materials which can be used in vivo and in vitro as structural supports for cells and tissues, frameworks for tissue formation and regeneration, or surfaces for cell contact.

The perforated dermal matrix is made of a biodegradable porous polymeric material. Biodegradable porous polymeric matrices include porous matrices of natural fibers, porous matrices of absorbable synthetic fibers, porous composite matrices of natural and synthetic fibers, and decellularized animal tissue. Examples include collagen matrices and collagen-glycosaminoglycan matrices.

Collagen is a major protein component of bone, cartilage, skin, and connective tissue in animals. Collagen occurs in several types, having differing physical properties. The most abundant types are Types I, II and III. In an exemplary embodiment of the present invention, Type I collagen is used for preparing the biodegradable porous polymeric matrix. Collagen derived from any source is suitable for use in the compositions of the present invention, including insoluble collagen, collagen soluble in acid, in neutral or basic aqueous solutions, as well as those collagens that are commercially available. Typical animal sources for collagen include but are not limited to recombinant collagen, fibrillar collagen from bovine, porcine, ovine, caprine and avian sources as well as soluble collagen from sources such as cattle bones and rat tail tendon.

The term glycosaminoglycan or GAG describes hexosamine-containing polysaccharides. Another name often used for this class of compounds is mucopolysaccharides. Chemically, GAGs are alternating copolymers made up of residues of hexosamine glycosidically bound and alternating in a more or less regular manner with either hexuronic acid or hexose moieties. Various forms of GAG which may be suitable for use in the process include, but are not limited to, hyalauronic acid, chondroitin 6-sulfate, chondroitin 4-sulfate, heparin, heparin sulfate, keratin sulfate and dermatan sulfate. A preferred GAG for preparing the biodegradable porous polymeric matrix is chondroitin 6-sulfate.

A sheet of collagen matrix or collagen-glycosaminoglycan matrix may be produced from a process comprising the steps: (1) preparing a dispersion of collagen (for example, bovine tendon collagen); (2) optionally adding glycosaminoglycan (GAG) to the collagen dispersion; (3) lyophilizing the collagen or collagen/GAG dispersion to dryness; (4) optionally cross-linking the lyophilized collagen or collagen/GAG material; (6) optionally cutting the tissue into desired shapes and sizes; and (7) optionally sterilizing. The average pore size of the matrix is within the range of about 100 μm to about 600 μm, preferably about 20 μm to 200 μm, as calculated by stereology from scanning electron micrograph of the surface or cross section as described by Dagalakis et al. J. of Biomedical Materials Research 14:511 (1980).

Decellularized animal tissues comprise scaffolds made of naturally-occurring polymer. Decellularized animal tissues and decellularization processes are described in U.S. Pat. Nos. 9,011,895, 7,354,702, and 6,696,074, which are all incorporated herein by reference. The patents describe methods of forming and preserving a bioremodelable, biopolymer scaffold material by subjecting animal tissue, for example fetal or neo-natal bovine dermis tissue, to chemical and mechanical processing.

A tissue regeneration matrix of the present invention, in the form of a sheet of biodegradable porous polymeric matrix, has a plurality of channels penetrating through the thickness of the sheet creating void areas on the sheet. The sheet may be flat or have a uniform thickness but it does not have to. The channels may penetrate vertically through the thickness of the sheet, but it is contemplated that the channels do not need to be perpendicular to the surface. They may have a slant or pass through the sheet at an angle.

Channels in matrices may be arranged in varying channel shapes, channel sizes, channel spacings, and void space percentages. Channel spacing refers to the distance between the centers of adjacent channels. A void space percentage, or also referred to as an open space percentage, is the percentage of channels' total void space or extracted material relative to the total area of an intact matrix.

The channels each may have a cross-section shape that is circular, elliptical, trapezoidal, square, rectangular, rhombus, polygonal, star-shaped, or the like, or a shape that is generally or substantially any of the foregoing. The channels may also have a cross-section that is custom shaped or irregular. Each channel may have uniform cross-sections but varying cross-sections are also contemplated.

Figure 1:
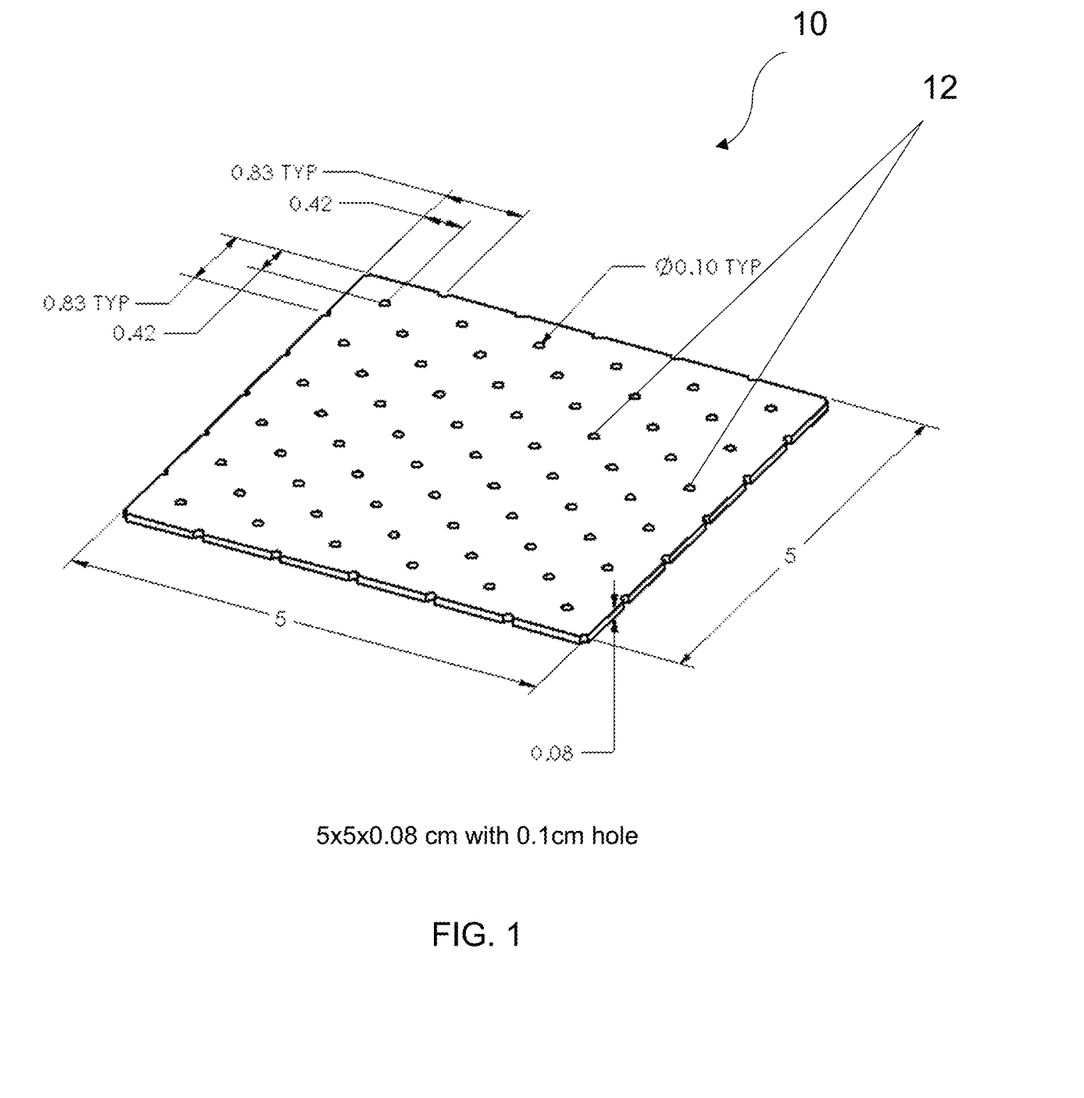
FIG. 1 illustrates a first embodiment of the matrix of the present invention.
Figure 2:
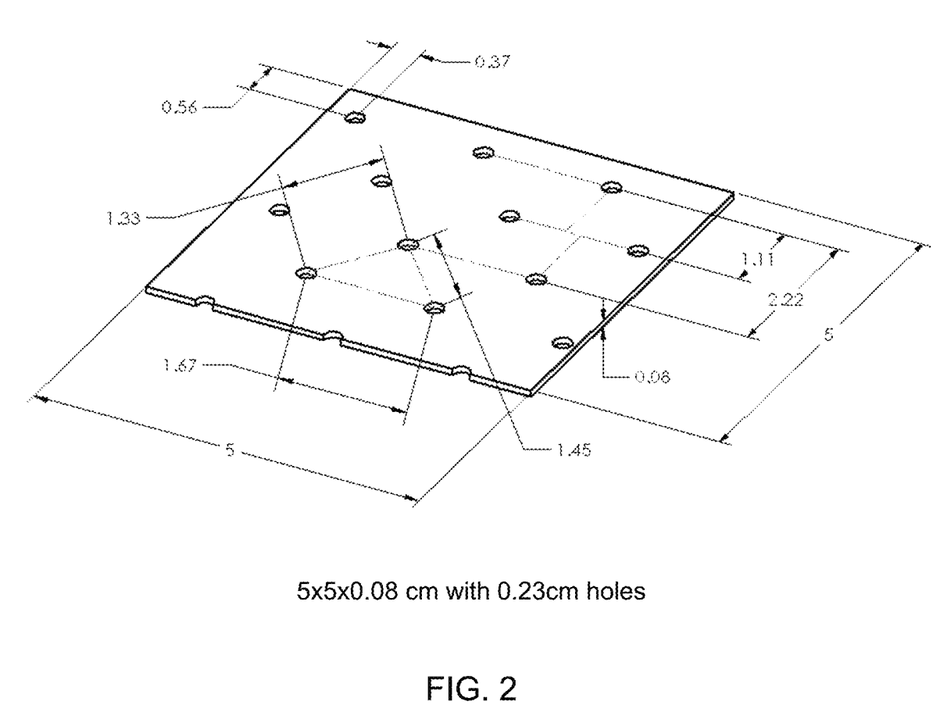
FIG. 2 illustrates a second embodiment of the matrix of the present invention.
Figure 3:
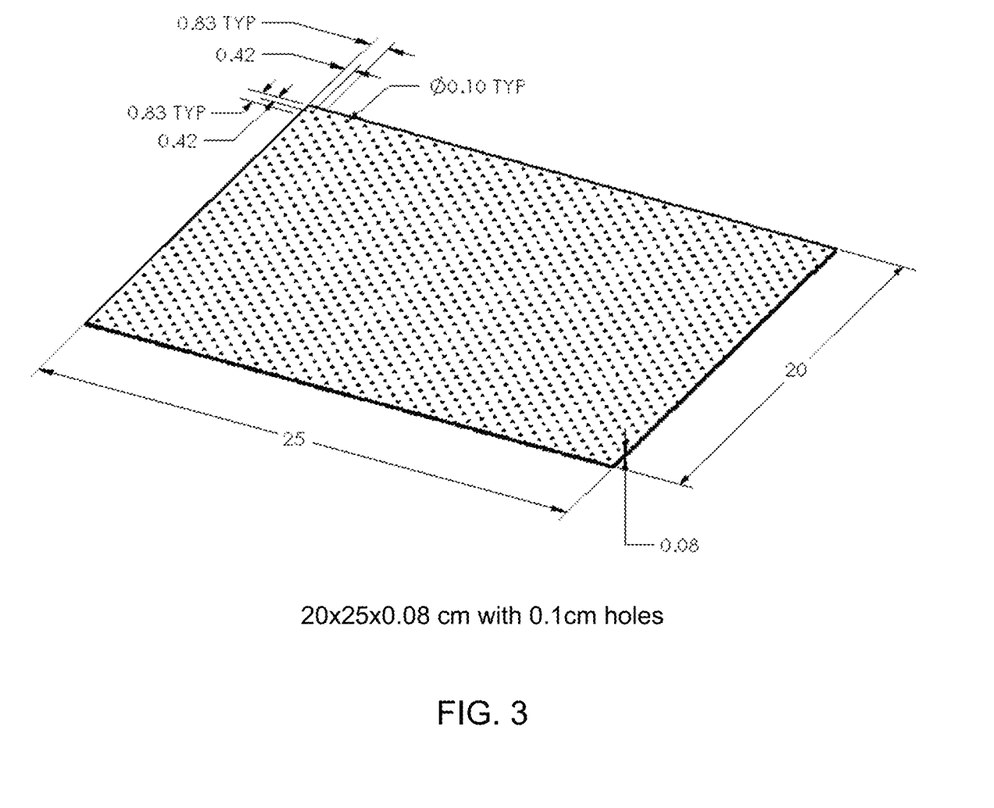
FIG. 3 illustrates a third embodiment of the matrix of the present invention.
Figure 4:
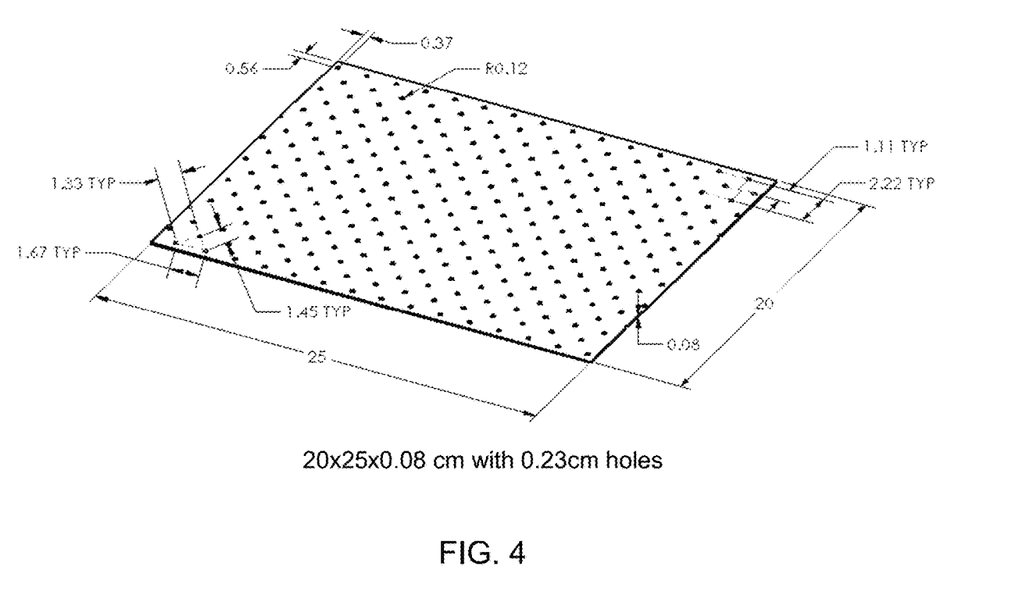
FIG. 4 illustrates a fourth embodiment of the matrix of the present invention.

FIGS. 1-4 illustrate exemplary embodiments of the perforated dermal regeneration matrix of the present invention. The examples illustrate small (5×5 cm) and large (20×25 cm) sizes and each matrix is shown in 2 channel sizes (1 mm and 2.3 mm). In more detail, the perforated dermal regeneration matrix 10 illustrated in FIG. 1 is 5×5 cm having a thickness of 0.08 cm and having a plurality of channels or macro-channels 12 of 1 mm in diameter arranged in staggered rows. In each row, adjacent channels have a channel spacing of 0.83 cm. Likewise, in each column, adjacent channels have a channel spacing of 0.83 cm. The TYP in the drawings refers to "typical", indicating the same dimensions apply to the other similar features in the drawings. It is contemplated that the diameter of the channels is in the range of about 0.25 mm to about 3 mm, preferably from about 0.5 mm to about 2.8 mm, and more preferably from about 0.8 mm to about 2.5 mm.

For channels in other shapes, the sizes of the channels are in the ranges equivalent to the sizes represented by the diameter ranges above. For example, such other shapes have at least one dimension in the range of about 0.25 mm to about 3 mm, preferably from about 0.5 mm to about 2.8 mm, and more preferably from about 0.8 mm to about 2.5 mm. The void area of each channel is in the range of 0.1 $mm^2$ to 7.0 $mm^2$, preferably 0.2 $mm^2$ to 6.2 $mm^2$, and more preferably 0.5 $mm^2$ to 5.0 $mm^2$.

Channels are separated from each other by a distance or spacing between 1 mm and 25 mm, (preferably between 5 mm and 15 mm). The number, size and spacing of matrix channels are configured to maintain a desired void space percentage, and to allow free movement of tissue-fluid exudate and maximally encourage even distribution of vascular tissue growth within the matrix.

The channels create void areas on the sheet. A void space percentage is the total void areas represented by the channels relative to the total area of the sheet in its intact or unperforated form without being stretched or expanded. The number, size and spacing of the channels are selected such that the void space percentage is in the range of 1% to 10%, preferably 1.5% to 5%, and more preferably 2% to 3%. The void space is selected to promote vascularization without compromising the integrity of the matrix or the benefit of the porous scaffold that supports cell penetration and vascular growth. The preclinical studies using matrices with channels in a single-stage procedure have shown significantly higher vascularization than solid configuration without channels.

The channels have a size and shape and are arranged with spacings and in a pattern such that the matrix promotes vessel growth. The channels may be arranged in a variety of patterns, regular or irregular. For example, the channels may be arranged on the matrix in staggered or aligned rows. The rows may be substantially parallel to each other, and the columns of the channels may also be substantially parallel to each other, but it is understood that they don't have to be parallel. The channels may be evenly or regularly spaced and substantially on the entire surface of the matrix or a substantial portion or any portion of the surface. Irregular channel distributions and combinations of different channel shapes and/or channel sizes are also contemplated.

The matrix has a thickness in the range of about 0.3 mm to about 4.0 mm, and preferably in the range of 0.5 mm to about 2.0 mm.

Perforation of the tissue graft is performed using a perforation machine that comprises a cutting die having a surface of desired dimensions. The cutting die has on its surface punches that have shapes and sizes that correspond to the predetermined shapes and sizes of the perforations on the tissue graft to be prepared. The punches are distributed in a pattern that correspond to the predetermined perforation pattern of the tissue graft to be prepared. Suitable perforation machines include those for industrial use.

Channels are introduced to the collagen-GAG matrix, either in its non-crosslinked state or in the dry/wet crosslinked state, utilizing mechanical means or a thermal laser. Mechanical means includes a mechanical perforation machine that comprises a cutting die having a surface of desired dimensions. The cutting die has on its surface punches that have shapes, sizes and spacings that correspond to the predetermined shapes, sizes and distribution pattern of the channels to be generated. Channels can also be introduced by using a laser beam, which usually can produce perforations in a predetermined pattern accurately and does not induce mechanical stresses on the material.

For clarity, the channels, or macro-channels, in the matrices in accordance with the present invention are different from the pores present in the porous matrices. Pores are formed by the arrangement of the fibers present in the matrix, for example, collagen fibers in a collagen matrix, during the manufacturing process of the matrix, whereas the channels are formed in the matrix and pass through the matrix after the matrix is formed, by utilizing mechanical means or a laser device to create channels that pass through the matrix as described above. At a microscopic level, pores are randomly oriented and acts as a scaffold that guides cell growth and tissue regeneration, as described in U.S. Pat. No. 4,947,840.

The matrices with channels of the present invention is useful for tissue regeneration such as skin regeneration. The matrices can be used for the management of wounds, including, without limitation, partial and full-thickness wounds, pressure ulcers, venous ulcers, diabetic ulcers, chronic vascular ulcers, tunneled/undermined wounds, surgical wounds (donor sites/grafts, post-Moh's surgery, post-laser surgery, podiatric, wound dehiscence), trauma wounds (abrasions, lacerations, burns including second and third degree burns, skin tears) and draining wounds. For example, the matrices can be used for the postexcisional treatment of full-thickness and partial-thickness injuries, such as deep partial-thickness thermal injuries, where sufficient autograft is not available at the time of excision or not desirable due to the physiological condition of the patient. The matrices can also be used for the repair of scar contractures, especially when donor sites for repair are not sufficient or desirable due to the physiological condition of the patient, or for use in reconstruction of postexcisional, full-thickness defects of the integument where there is, in the opinion of the treating surgeon, a potential benefit to the patient by improving the reconstructive outcome or decreasing their mortality/morbidity.

In using the matrix of the present invention on a patient who is in need of wound management, first prepare wound bed using standard methods to remove any debris and necrotic tissue, and surgically debride the wound as needed, to the level that the wound edges contain viable tissue, and then cut the matrix to size and apply to the wound bed.

Optionally, depending on the severity of the wound and the physiological conditions of the patient, a skin autograft can be placed on the matrix that has been applied to the wound bed. In this step, a thin epidermal or split-thickness autograft is taken from a donor site. Split-thickness skin grafts may be harvested in conventional ways, for example, using a surgical knife, or manual or powered dermatome. The harvested skin graft may be meshed by conventional methods, for example, using a surgical scalpel or a manual or powered mesher. A mesher is usually used by applying multiple slits at regular intervals and in preset ratios, for example, 3/8 to 1, 1 to 1, 2 to 1, 3 to 1, and 6 to 1. Meshing a skin graft allows the graft to stretch and increases the area it can cover. A higher meshing ratio means a higher level a skin graft can stretch, but it will likely take longer for the wound to heal completely due to the increased area to epithelialize.

After application of the matrix of the present invention and the skin graft, use appropriate secondary dressings to maintain dressing adherence and protect the wound area. Examples of secondary dressings including antimicrobial dressings, negative pressure wound therapy, bulky gauze, compression layers, other suitable materials, or combinations of the foregoing. The optimum secondary dressing is determined by wound location, size, depth and user preference. Change the secondary dressing as needed. Frequency of secondary dressing change will be dependent upon volume of exudate produced, type of dressing used and the clinician's need to inspect the wound bed for signs of infection or healing.

In another aspect of the present invention, a surgical kit is provided which comprises a tissue regeneration matrix with channels of the present invention in combination with a surgical tool for harvesting thin slices of skin from a donor site to produce skin grafts. Examples of such surgical tool include, but are not limited to, manual or air or electric powered dermatomes.

EXAMPLES

The examples are specific embodiments of the present invention but are not intended to limit it.

EXAMPLE 1. Preparation of Collagen/GAG Matrix

Glycosaminoglycan (chondroitin-6-sulfate) solution in acetic acid is prepared by mixing 828 grams of deionized water with 2.5 mL of glacial acetic acid and adding to the mixture 2.2 grams of chondroitin-6-sulfate (dry weight). The solution is stirred until the chondroitin-6-sulfate is completely dissolved, preferably for about one hour.

A collagen dispersion of 0.5% collagen in 0.05 M acetic acid is prepared in a mixing vessel with a cooling system cooled to 4° C. Deionized water (4153 grams) is added to the mixing vessel followed by 12.5 mL of acetic acid and the solution is mixed for ten minutes. Purified collagen (25 grams dry weight) is cut into pieces not larger than 1 cm.sup.2 and mixed for 5 minutes at 1 to 10° C. at 25 Hz. The emulsifier and disperser is then increased to approximately 50 Hz and run for 30 minutes while maintaining a temperature of <25° C.

While continuing to emulsify and disperse, the chondroitin-6-sulfate solution is then added over a time period of 50 minutes. After the addition is complete, the dispersion is mixed for another hour, while maintaining the temperature at <25° C. After mixing for one hour, the emulsifier and disperser are turned off and the dispersion is degassed under vacuum for 30 minutes.

The dispersion is then poured into trays and lyophilized for 24 hours. After the lyophilization is completed, the trays are placed in a vacuum oven and subjected to dehydrothermal treatment at 105° C. for 16 hours under vacuum. After the dehydrothermal treatment, the collagen/GAG matrices can either be directly cross-linked.

The standard cross-linking procedure is carried out in a solution of 0.25% glutaraldehyde in 0.3% acetic acid. During the procedure, the collagen/GAG matrix can be fixed in a suitable frame that holds the matrix in place in the cross-linking solution or, in a lab scale, the cross-linking can be done with the matrix floating in the cross-linking solution. The cross-linking solution is prepared by adding the glutaraldehyde to 0.3% acetic acid solution in deionized water. The solution is allowed to stand for at least 30 minutes before adding the matrices. The matrices are kept in the solution for 20 to 24 hours. The glutaraldehyde solution is then removed and the matrices are washed three times with deionized water and allowed to soak in the deionized water for 1 to 2 hours each wash. Finally, the matrices are subjected to a final soak in deionized water for 16 hours.

EXAMPLE 2. Introduction of Channels to Collagen/GAG Matrix

Channels were introduced to the collagen-GAG matrix in its crosslinked wet state, utilizing mechanical means to produce. The matrices are cut to size if necessary, sterilized and stored until use. In one embodiment, eighteen channels of 2 mm diameter were created with a 2 mm biopsy punch in a 5 cm×5 cm matrix in a staggered pattern and generally evenly distributed in five rows. In this embodiment, the channels may be configured to maintain a void space percentage of 2.26%. This corresponds to a 50 mm×50 mm square device with 18 2 mm diameter channels as demonstrated by the following series of equations:

$$A_{C_o} = 18\pi\left(\frac{2 \text{ mm}}{2}\right)^2 \qquad (1)$$

-continued $$A_{D_o} = 50 \text{ mm} * 50 \text{ mm} = (50 \text{ mm})^2 \qquad (2)$$

$$P_V = \frac{A_{C_o}}{A_{D_o}} * 100\% = \frac{18\pi(2 \text{ mm})^2}{2^2(50 \text{ mm})^2} * 100\% = 2.26\% \qquad (3)$$

where $A_{C_o}$ is the combined area of the channels in the corresponding configuration, $A_{D_o}$ is the area of the device in the corresponding configuration and $P_V$ is the percent void space. This configuration may be generalized to produce any size device with different size holes. An equation used to determine the number of channels in a device is derived below:

$$\frac{A_{C_o}}{A_{D_o}} = \frac{A_C}{A_D} \qquad (4)$$

$$\frac{18\pi(2 \text{ mm})^2}{2^2(50 \text{ mm})^2} = \frac{N_C \pi \left(\frac{D_C}{2}\right)^2}{A_D} \qquad (5)$$

$$N_C = \frac{A_D 18\pi(2 \text{ mm})^2 2^2}{2^2 \pi (50 \text{ mm})^2 D_C^2} \qquad (6)$$

$$N_C = \frac{18}{625} * \frac{A_D}{D_C^2} \qquad (7)$$

where $N_C$ is the number of channels, $A_D$ is the area of the device, and $D_C$ is the diameter of the channels in mm.

EXAMPLE 3. Comparison of Matrices with and without Channels in Graft Take

Figure 5:
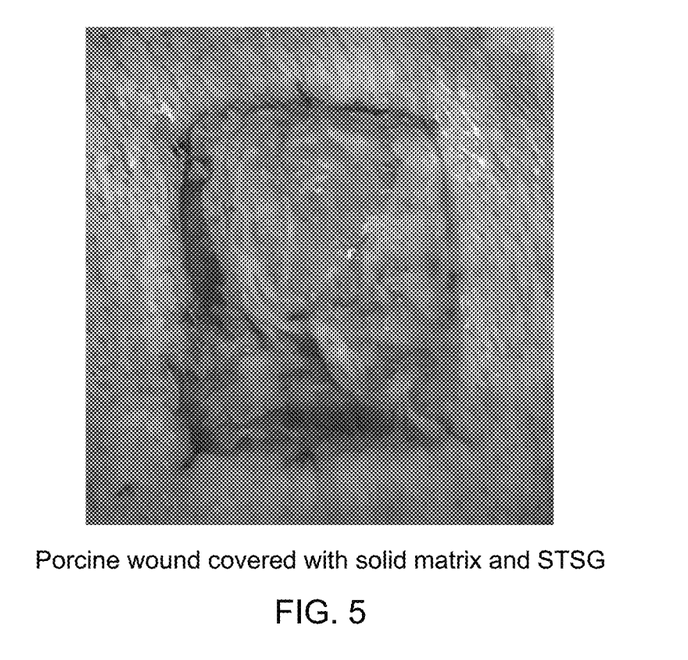
FIG. 5 is an in-life image of a skin graft sloughing over solid collagen matrix in a porcine wound model.
Figure 6:
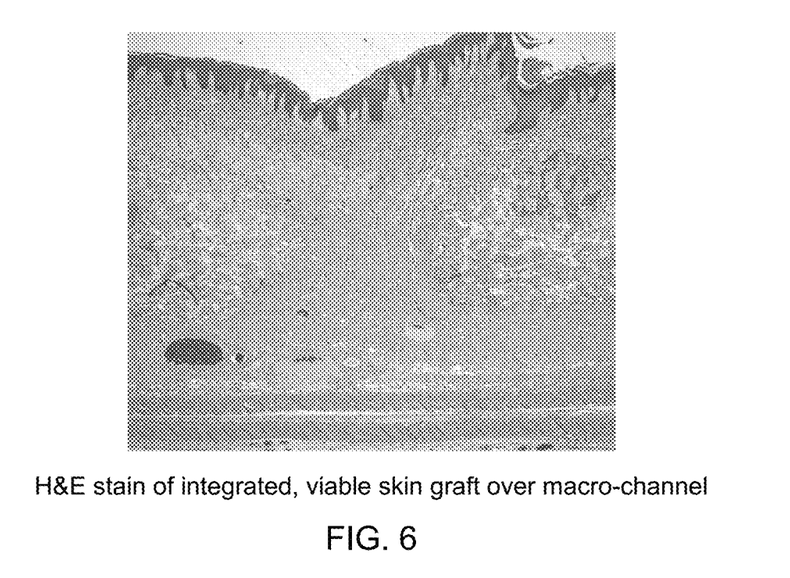
FIG. 6 is an H&E stained histology image showing integrated, viable skin graft over a macro-channel in a collagen matrix in accordance with the present invention.

The effect of introducing channels into a collagen-chondroitin-6-sulfate (C6S) matrix on STSG take was investigated and compared with a collagen-C6S matrix without channels. 4×4 cm full-thickness wounds were created on the dorsum of Yorkshire pigs. Eighteen channels of 2 mm diameter were created with a 2 mm biopsy punch in a 5 cm×5 cm matrix in a staggered pattern and generally evenly distributed in five rows. STSG was applied to the wounds directly over the matrix with and without channels. Dressing changes were performed at 3 to 4 day intervals up to sacrifice at Day 14. In prior studies, it has been observed that in the porcine wound covered with solid matrix and split thickness skin graft (STSG), the autograft becomes necrotic and sloughs by Day 11, as shown in FIG. 5. In contrast, the autograft is well integrated when macro-channels are introduced into the matrix. As shown in FIG. 6, at 14 days histology showed that granulation tissue formed within the channels provide sufficient blood supply and nutrients to the overlying STSG, thereby enhancing graft survival.

Channels in the collagen-chondroitin-6-sulfate matrix increased autograft take in a single stage procedure.

EXAMPLE 4. Evaluation of Impact of Channels in Matrix on Graft Survival

The effect of introducing 5, 9 or 18 channels into a collagen-chondroitin-6-sulfate matrix on STSG take was investigated to evaluate the impact of channel density on graft survival. The channels were regularly distributed on the matrix. Full-thickness wounds (4×4 cm) were created on the dorsum of Yorkshire pigs. On Day 0, wounds received a 5 cm² piece of collagen matrix with 5, 9, or 18 equidistant 2 mm diameter channels followed by a 0.012-inch-thick split thickness skin autograft (STSG). Treatments were sutured to adjacent skin wound margins, then covered with moist bolster dressing. Dressings were changed every 3 or 4 days and gross observations, wound size/area measurements, and digital images were acquired. All pigs were euthanized on Day 14. At Day 14, all wounds were completely re-epithelialized, had complete matrix take and comparable inflammatory cell types and numbers. Control wounds that were only STSG treated had more precontraction-type (scar) granulation tissue than collagen-chondroitin-6-sulfate matrix treated wounds. All wounds treated with matrix containing channels and STSG had less contraction than control wounds treated with STSG-only. The highest density of channels did not diminish the ability of matrix to inhibit contraction by acting as a space occupying mass. The study showed that channels in the collagen-chondroitin-6-sulfate matrix increased autograft take.

EXAMPLE 5. Impact of Channel Sizes on Graft Take

Figure 7A:
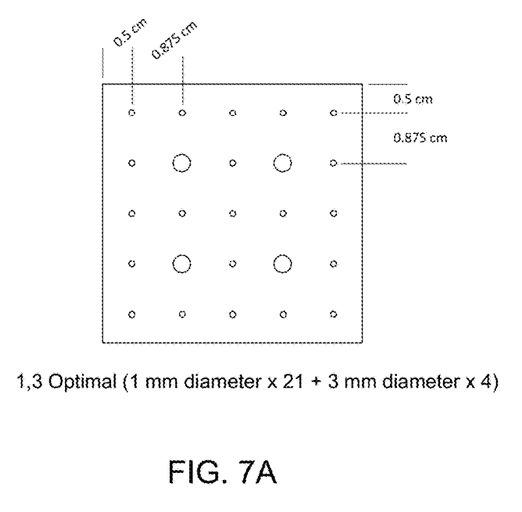
FIGS. 7A to 7D illustrate various embodiments used in preclinical studies.
Figure 7B:
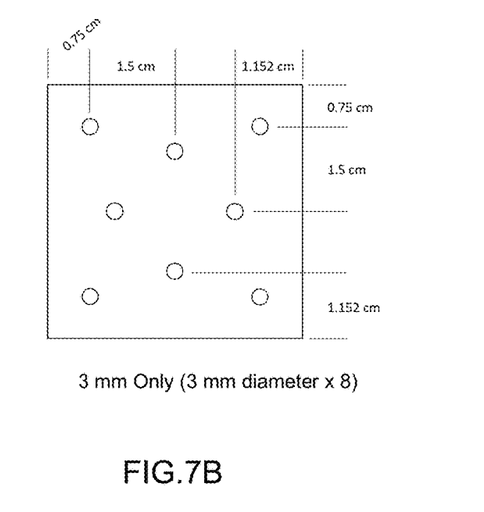
Figures 7C, 7D:
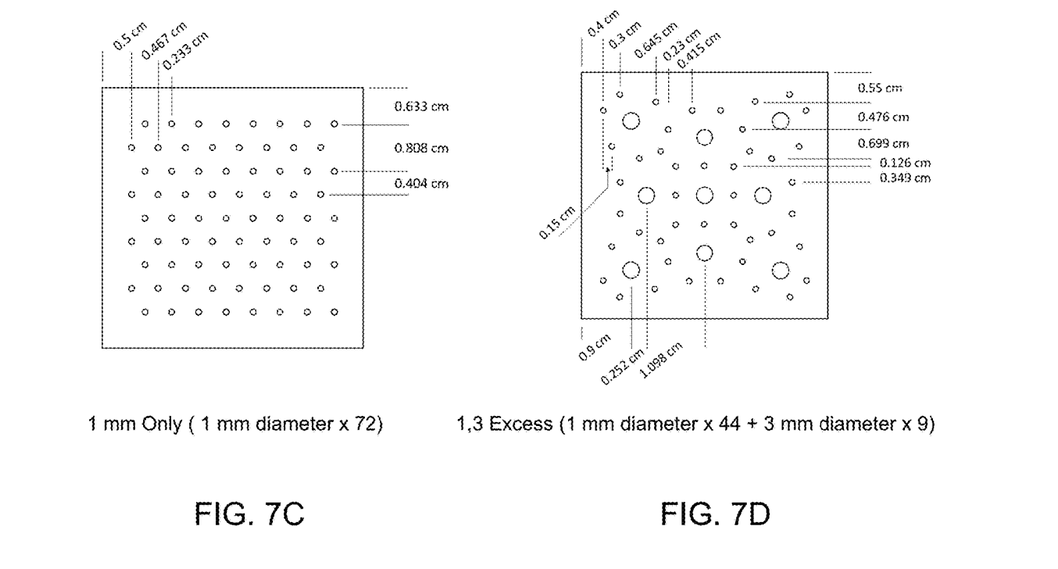

The impact of channels in collagen matrices on autograft take, contracture, early vascularization, granulation bed, and epithelialization via histology was investigated in a porcine full thickness wound model in the following six experimental groups: (1) matrix with 21 channels of 1 mm diameter and 4 channels of 3 mm diameter (1,3 Optimal, illustrated in FIG. 7A) and STSG, (2) matrix with 8 channels of 3 mm channels (3 mm Only, illustrated in FIG. 7B) and STSG, (3) matrix with 72 channels of 1 mm diameter (1 mm Only, illustrated in FIG. 7C) and STSG, (4) matrix with 44 channels of 1 mm diameter and 9 channels of 3 mm diameter)(1,3 Excess, illustrated in FIG. 7D) and STSG, (5) matrix without any channels and with STSG, and (6) STSG only. The 1 and 3 mm channels were created in the matrices using biopsy punches of 1 and 3 mm respectively. Eight full-thickness wounds (4×4 cm) were created in each of the five Yorkshire-cross pigs used in the study. STSG pieces were collected from a donor site using one pass of the ZIMMER electric dermatome set at 0.012' thickness with a 7 cm blade immediately prior to application into the wound bed. All grafts were stored in sterile saline and kept on ice prior to application, if needed. On Day 0, the matrix for treatment was applied to the wound bed and then STSG was placed on the matrix, as applicable in each experimental group. The matrices and STSG were sutured to the wound site. Dressings and bandages were applied to the wounds, and the dressings were changed on Day 3. Wound measurements were taken on Day 0 and Day 8. 2D imaging was taken on Days 0, 3 and 8. Wounds were also excised on Day 8 for histological analysis.

Figure 8A:
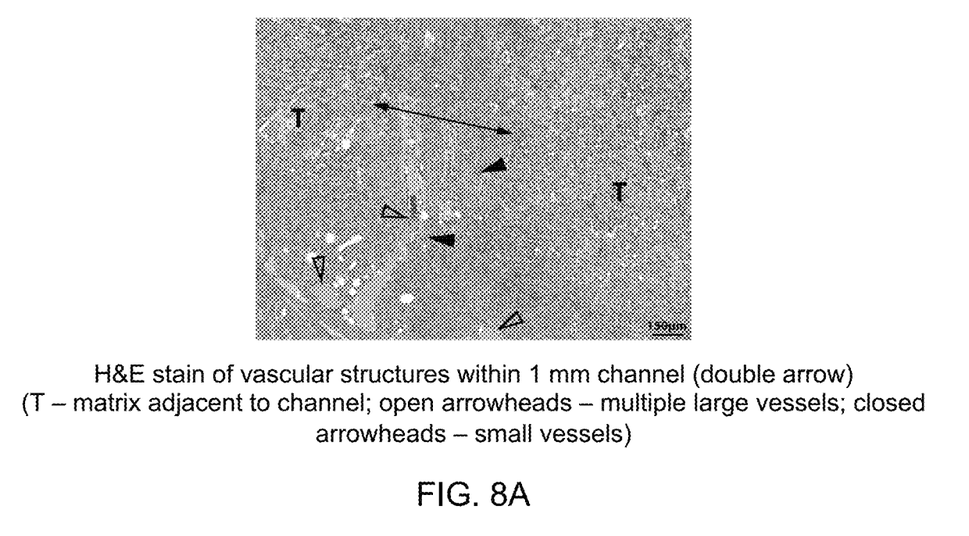
FIG. 8A shows H&E stain of vascular structures within 1 mm channel (double arrow) (T—matrix adjacent to channel; open arrowheads—multiple large vessels; closed arrowheads—small vessels)
Figure 8B:
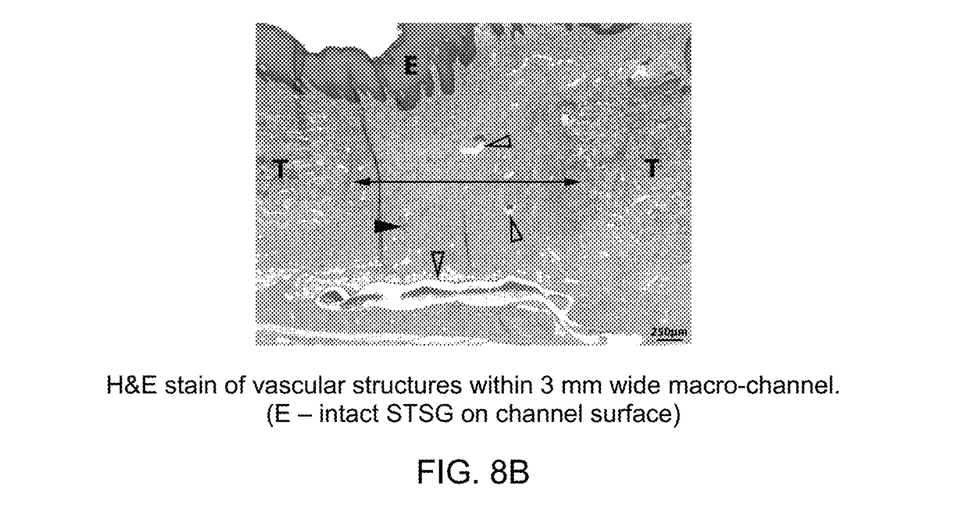
FIG. 8B shows H&E stain of vascular structures within 3 mm wide macro-channel (E—intact STSG on channel surface)
Figure 9:
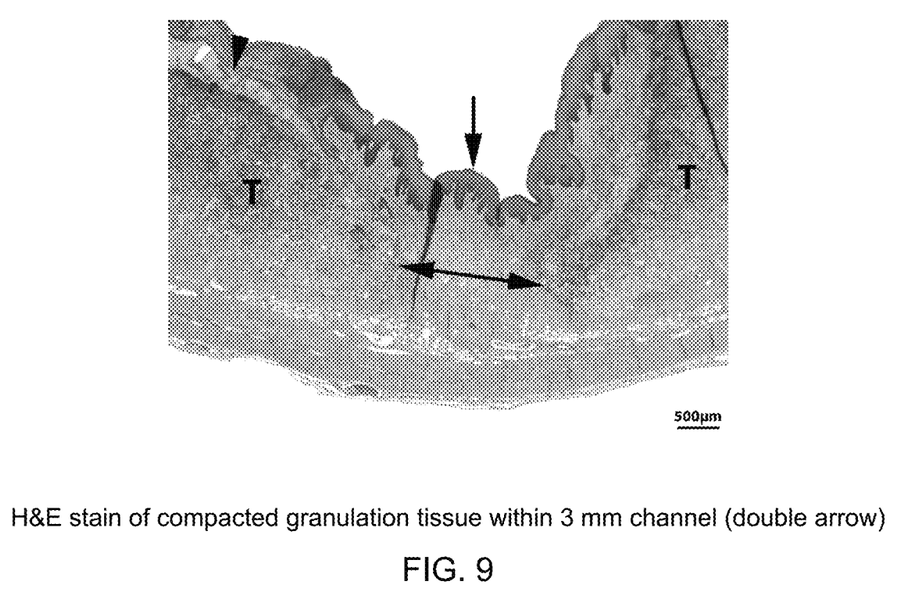
FIG. 9 is a H&E stain image of compacted granulation tissue within 3 mm macro-channel (double arrow)

Vascularization within the 1 mm and 3 mm channels was assessed to determine the approximate overall numbers of small and large vessels within the granulation tissue that was infiltrating into the channels (FIGS. 8A & 8B). The 1 mm TG+STSG appeared to have the most ideal vascular pattern, with the greatest average score for large vessels within the channels. The most desirable outcome (minimal contraction, good autograft take) occurred in the matrix with 1 mm channels+STSG group. The 1 mm, 3 mm Excess+STSG group maintained similar graft take but had an increase in contraction. Contraction of the tissue within channels appeared to directly correlate with the size of the channels, with the 3 mm channels having a greater propensity to cause contraction of the wound bed compared to the 1 mm channels (FIG. 9).

EXAMPLE 6. Impact of Matrix Channels on Vascularization

Figure 10:
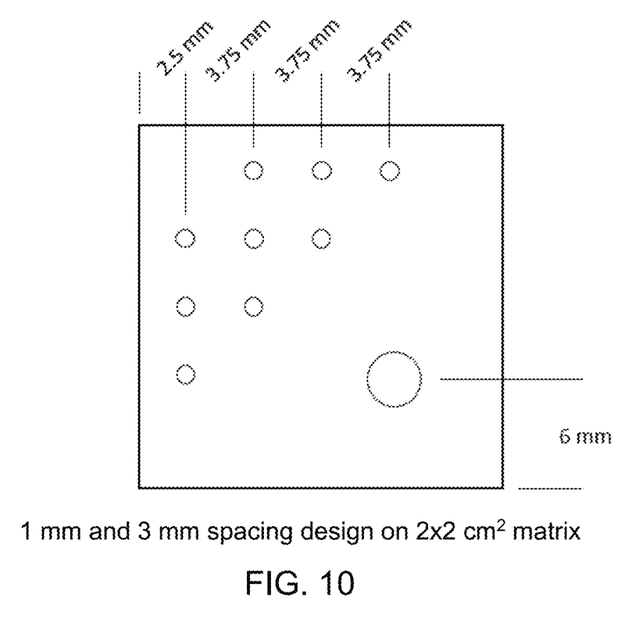
FIG. 10 illustrates the embodiment used in the intra-abdominal preclinical study.

The influence of channel diameter in a dermal substitute on vascular ingrowth was investigated. Anesthetized rats (n=18) had 2×2 cm² matrix intra-abdominally bilaterally implanted onto ventral peritoneum with excoriated serosa. The matrix was perforated with either 1 and 3 mm diameter channels or 1 mm diameter channels with varied spacing (FIG. 10). At days 8 and 22 post-implantation, four animals/timepoint were perfused with a vascular imaging agent (AltaBlue), followed by abdominal CT and micro-CT. The remaining animals were sacrificed for histological analysis.

Figure 11:
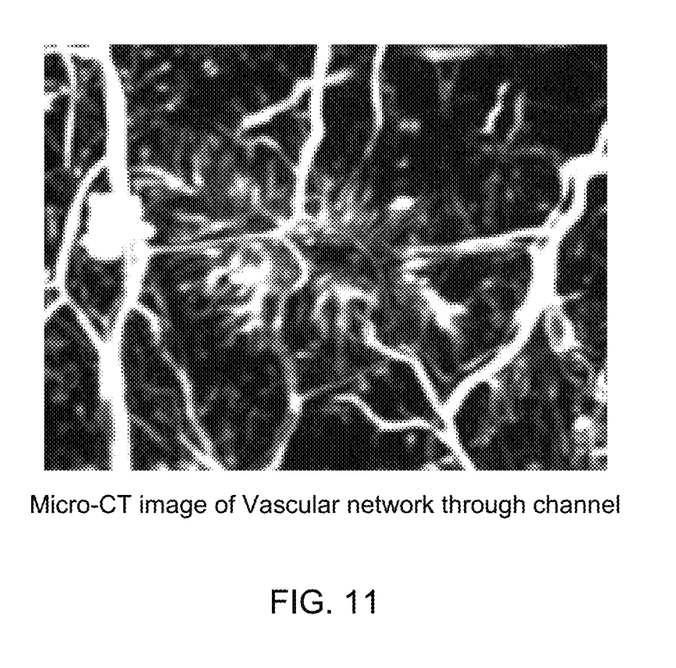
FIG. 11 shows micro-CT imaging of a vascular network within a macro-channel.
Figure 12A:
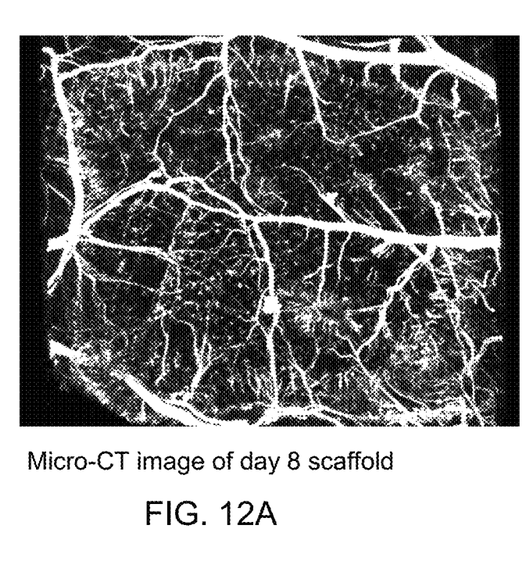
FIGS. 12A and 12B show micro-CT images of the entire intra-abdominally implanted matrix at day 8 and day 22, respectively.
Figure 12B:
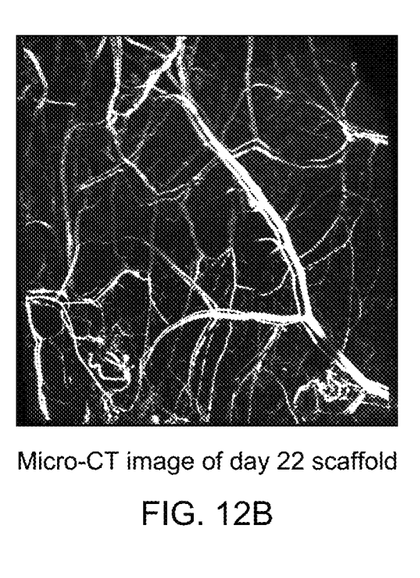

At Day 8, micro-CT analysis showed that macro-channels within the CC6S matrix facilitated the rapid growth of vascular networks through the scaffold (FIG. 11). Vascular networks that develop in 1 mm channels originate from a primary feeder vessel whereas networks in 3 mm channels utilize multiple feeder vessels. Vessels within vascular networks that develop through 3 mm channels are larger while the vascular networks through 1 mm channels resemble capillary networks. At Day 22, scaffolds were less conspicuous, and channels were not visible by microCT (FIGS. 12A & 12B).

Figure 13:
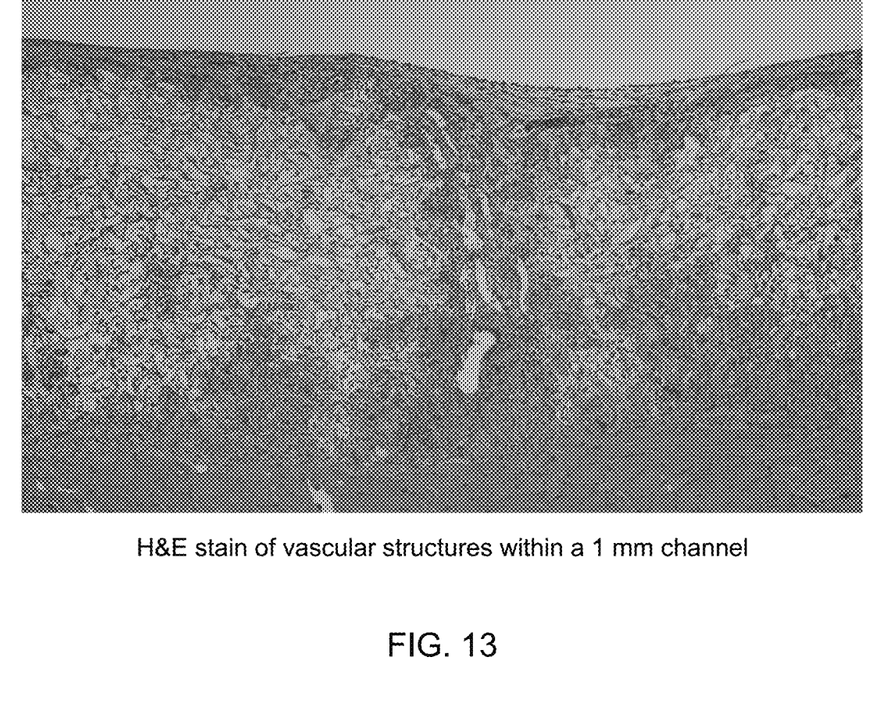
FIG. 13 is an H&E stain image of vascular structures within a 1 mm macro-channel of an intra-abdominally implanted matrix.

In this intra-abdominal model, the matrix insulates the abdominal contents from the acute inflammation that arise from the excoriated peritoneum. Histological analysis confirmed that channels create openings for inflammatory mediators and vessels to access the matrix outer surface resulting in increased remodeling in and around the channels. The 1 mm channels contained a thin vessel rimmed by maturing fibrous connective tissue, whereas the 3 mm channels usually contained a vessel that was dilated. In terms of ability to support blood flow, both channels performed similarly (FIG. 13). At Day 22, the matrix was remodeled such that the defining features became indistinguishable from native tissue. Both 1 and 3 mm channels provide adequate space for vascularization. However, to optimize dermal healing outcome (low scarring), preservation of matrix collagen is critical. Therefore, smaller channels are likely to be more beneficial since they will maximize collagen content while enhancing vascularity and STSG survival.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

What is claimed is:

1. A method of treating a skin wound of a mammalian subject in need of such treatment, the method comprising:
   providing a sheet of biodegradable porous polymeric matrix, wherein the sheet comprises:
   a plurality of channels that are distributed on the matrix in staggered or aligned rows and penetrate through a thickness of the sheet, thereby creating void areas in the sheet, each of the plurality of channels having a cross-section shape that is generally circular, elliptical, trapezoidal, rectangular, rhombus, polygonal, star-shaped, custom shaped, or irregular;
   a void space percentage of 1% to 10%, the void space percentage being total void areas represented by the plurality of channels relative to the total area of the sheet without the plurality of channels formed therein;
   cleaning the skin wound to provide a prepared wound bed;
   placing the sheet of biodegradable porous polymeric matrix onto the prepared wound bed;
   removing a skin graft from a healthy area of the subject and placing the skin graft on top of the sheet of biodegradable porous polymeric matrix on the prepared wound bed; and
   closing the skin wound after the sheet of biodegradable porous polymeric matrix and the skin graft have been placed on the prepared wound bed.

2. The method of claim 1, wherein a quantity and a size of each of the plurality of channels is selected such that the void space percentage is in a range of 1.5% to 5%.

3. The method of claim 1, wherein a quantity and a size of each of the plurality of channels is selected such that the void space percentage is in a range of 2% to 3%.

4. The method of claim 1, wherein the biodegradable porous polymeric matrix is selected from the group consisting of porous matrices of natural fibers and porous matrices of absorbable synthetic fibers.

5. The method of claim 1, wherein the biodegradable porous polymeric matrix is a collagen-glycosaminoglycan matrix.

6. The method of claim 1, wherein each of the plurality of channels has a substantially circular cross-section.

7. The method of claim 6, wherein each of the plurality of channels has a diameter of about 0.5 mm to about 2.8 mm.

8. The method of claim 6, wherein each of the plurality of channels has a diameter of about 0.8 mm to about 2.5 mm.

9. The method of claim 1, wherein the rows in which the plurality of channels are arranged are substantially parallel to each other.

10. The method of claim 1, wherein the plurality of channels are evenly spaced substantially over an entire surface of the biodegradable porous polymeric matrix.

11. The method of claim 1, wherein the biodegradable porous polymeric matrix has a thickness in a range of about 0.3 mm to about 4.0 mm.

12. The method of claim 1, wherein the biodegradable porous polymeric matrix has a thickness in a range of about 0.5 mm to about 2.0 mm.

13. The method of claim 1, wherein the skin wound is selected from the group consisting of partial and full-thickness wounds, pressure ulcers, venous ulcers, diabetic ulcers, chronic vascular ulcers, surgical wounds, trauma wounds, and draining wounds.

14. The method of claim 1, wherein the skin wound is a full-thickness skin wound or a deep partial-thickness skin wound.

* * * * *

UNITED STATES PATENT AND TRADEMARK OFFICE
CERTIFICATE OF CORRECTION

PATENT NO. : 12,059,509 B1
APPLICATION NO. : 16/866966
DATED : August 13, 2024
INVENTOR(S) : Kenneth Burhop et al.

Page 1 of 1

It is certified that error appears in the above-identified patent and that said Letters Patent is hereby corrected as shown below:

In the Specification

Column 1 Line 38:
"A product commercially available on the market is INTEGRAL® Dermal"

Should be:
-- A product commercially available on the market is INTEGRA® Dermal --.

Column 9 Line 22:

"
$$N_C = \frac{A_D 18\pi(2\,mm)^2 2^2}{2^2 \pi(50\,mm)^2 D_C^2} \quad (6)$$

$$N_C = \frac{18}{625} * \frac{A_D}{D_C^2} \quad (7)$$
"

Should be:

-- 
$$N_C = \frac{A_D 18\pi(2mm)^2 2^2}{2^2 \pi(50mm)^2 D_C^2} \quad (6)$$

$$N_C = \frac{18}{625} * \frac{A_D}{D_C^2} \quad (7)$$
 --.

Signed and Sealed this
Twenty-second Day of April, 2025

Coke Morgan Stewart
*Acting Director of the United States Patent and Trademark Office*